(12) United States Patent
Halliburton et al.

(10) Patent No.: US 11,133,699 B2
(45) Date of Patent: Sep. 28, 2021

(54) CHARGING SYSTEMS FOR DEVICES RELATED TO DIALYSIS TREATMENTS

(71) Applicant: Fresenius Medical Care Holdings, Inc., Waltham, MA (US)

(72) Inventors: Donovan Halliburton, Martinez, CA (US); Alexander Joseph Brown, Danville, CA (US); Kelly Yik, Hayward, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 17/010,627

(22) Filed: Sep. 2, 2020

(65) Prior Publication Data

US 2020/0403447 A1 Dec. 24, 2020

Related U.S. Application Data

(63) Continuation of application No. 16/262,249, filed on Jan. 30, 2019, now Pat. No. 10,804,730, which is a
(Continued)

(51) Int. Cl.
*H02J 7/02* (2016.01)
*H02J 50/10* (2016.01)
*A61M 1/14* (2006.01)
*A61M 1/28* (2006.01)
*H02J 7/00* (2006.01)

(52) U.S. Cl.
CPC ............... *H02J 7/025* (2013.01); *A61M 1/14* (2013.01); *A61M 1/28* (2013.01); *H02J 7/0068* (2013.01); *H02J 50/10* (2016.02); *A61M 2205/04* (2013.01); *A61M 2205/18* (2013.01); *A61M 2205/3592* (2013.01); *A61M 2205/52* (2013.01);
(Continued)

(58) Field of Classification Search
CPC .......................................................... H02J 7/00
USPC .......................................................... 320/108
See application file for complete search history.

(56) References Cited

U.S. PATENT DOCUMENTS 8,284,046 B2 10/2012 Allen et al.
8,428,676 B2 4/2013 McKenna et al.
(Continued)

FOREIGN PATENT DOCUMENTS

CN 101505812 8/2009
CN 104271175 1/2015
(Continued)

OTHER PUBLICATIONS

PCT International Preliminary Report on Patentability in International Application No. PCT/US2016/060978, dated May 15, 2018, 10 pages.
(Continued)

*Primary Examiner* — Robert Grant
(74) *Attorney, Agent, or Firm* — Fish & Richardson P.C.

(57) ABSTRACT

In one aspect of the invention, a method of charging a medical device includes receiving radiofrequency signals from a remote machine remote from the medical device via a receiver of the medical device. The method includes converting the radiofrequency signals into electrical energy via a generator of the medical device. The method includes storing the electrical energy in an energy cell of the medical device. The method also includes powering a power consumption component of the medical device by transmitting the energy from the energy cell to the power consumption component.

33 Claims, 8 Drawing Sheets

Related U.S. Application Data continuation of application No. 14/940,437, filed on Nov. 13, 2015, now Pat. No. 10,199,852.

(52) U.S. Cl.
CPC ............ *A61M 2205/8206* (2013.01); *A61M 2205/8237* (2013.01); *A61M 2205/8293* (2013.01)

(56) References Cited

U.S. PATENT DOCUMENTS

| | | |
|---|---|---|
| 8,512,553 B2 | 8/2013 | Cicchello et al. |
| 8,702,640 B2 | 4/2014 | Dacey et al. |
| 8,708,923 B2 | 4/2014 | Turicchia et al. |
| 10,199,852 B2 | 2/2019 | Halliburton et al. |
| 10,804,730 B2 | 10/2020 | Halliburton et al. |
| 2005/0101901 A1 | 5/2005 | Gura |
| 2008/0300660 A1 | 12/2008 | John |
| 2010/0094193 A1 | 4/2010 | Gura et al. |
| 2013/0131575 A1 | 5/2013 | Dacey, Jr. et al. |
| 2013/0292319 A1 | 11/2013 | Fulkerson et al. |
| 2014/0183106 A1 | 7/2014 | Kotsos et al. |
| 2015/0279186 A1 | 10/2015 | Chen et al. |
| 2017/0141601 A1 | 5/2017 | Halliburton et al. |
| 2019/0165597 A1 | 5/2019 | Halliburton et al. |

FOREIGN PATENT DOCUMENTS

| | | |
|---|---|---|
| CN | 104856695 | 8/2015 |
| CN | 104939804 | 9/2015 |
| CN | 204633363 | 9/2015 |
| WO | WO 2008/021462 | 2/2008 |
| WO | WO 2011/038353 | 3/2011 |
| WO | WO 2013/122580 | 8/2013 |
| WO | WO 2014/144070 | 9/2014 |
| WO | WO 2015/024647 | 2/2015 |
| WO | WO 2016/132187 | 8/2016 |

OTHER PUBLICATIONS

PCT International Search Report and Written Opinion in Application No. PCT/US2016/060978, dated Jan. 31, 2017, 12 pages.

CHARGING SYSTEMS FOR DEVICES RELATED TO DIALYSIS TREATMENTS

CROSS-REFERENCE TO RELATED APPLICATIONS

This application is a continuation application of and claims priority under 35 U.S.C. § 120 to U.S. application Ser. No. 16/262,249, filed on Jan. 30, 2019, which is a continuation application of U.S. application Ser. No. 14/940,437, filed on Nov. 13, 2015, now U.S. Pat. No. 10,199,852. The disclosure of each application is hereby incorporated by reference.

TECHNICAL FIELD

This disclosure relates to charging systems for devices related to dialysis treatments.

BACKGROUND

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing a dialysis solution or dialysate through the dialyzer. A permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), a patient's peritoneal cavity is periodically infused with sterile aqueous solution, referred to as PD solution or dialysate. The membranous lining of the patient's peritoneum acts as a natural permeable membrane that allows diffusion and osmosis exchanges to take place between the solution and the blood stream. These exchanges across the patient's peritoneum result in the removal of waste products, including solutes like urea and creatinine, from the blood, and regulate the levels of other substances, such as sodium and water, in the blood.

Many PD machines are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle.

Various auxiliary medical devices may be used contemporaneously with dialysis treatments to check the status and progress of the blood or fluid filtration processes. The auxiliary medical devices may include wearable or implantable devices powered by a battery such as a coin cell lithium battery. A coin cell lithium battery has a limited amount of available energy. When such a battery is contained within a human implantable device, the battery is general sealed within the device in order to allow for water ingress protection. Therefore, after a period of time, the battery is drained and the entire device must be replaced. For patients that intend to use the device for many years, the device must be replaced many times. This increases the overall cost of using the device per patient. Furthermore, the size and weight of the device is adversely impacted by the size of the battery. Large size batteries are required for longer periods of operational lifetime. However, increasing the battery size disadvantageously limits patient mobility and the ability to implant the device.

SUMMARY

In one aspect of the invention, a method of charging a medical device includes receiving radiofrequency signals from a remote machine remote from the medical device via a receiver of the medical device. The method includes converting the radiofrequency signals into electrical energy via a generator of the medical device. The method includes storing the electrical energy in an energy cell of the medical device. The method also includes powering a power consumption component of the medical device by transmitting the energy from the energy cell to the power consumption component.

In some implementations, the remote machine is a dialysis machine. Powering the power consumption component of the medical device may include applying power to an electrode of the medical device to detect an electrical property related to a wetness state. Powering the power consumption component of the medical device includes testing a property of blood with the medical device, in particular implementations. The method includes receiving distinct energy types from distinct energy sources positioned remote from the medical device via the receiver, in some implementations. The method may include converting the distinct types of energy into electrical energy via the generator. In some implementations, receiving distinct energy types includes receiving energy selected from the group consisting of: radiofrequency signals, thermal energy, light energy, and kinetic energy. Receiving distinct energy types may include receiving energy via a thermocouple. Receiving distinct energy types may include receiving energy via a photosensor. Receiving distinct energy types may include receiving energy via a microelectromechanical system (MEMS) device.

In another aspect of the invention, a medical system includes a receiver configured to wirelessly receive energy from at least one distinct energy source emitting a distinct type of energy. The medical system includes a generator coupled to the receiver. The generator is configured to convert the distinct type of energy into electrical energy. The medical system also includes an energy cell coupled to the generator. The energy cell is configured to store the electrical energy. The medical system includes a power consumption component communicably coupled to the energy cell to consume the stored electrical energy.

In some implementations, the power consumption component includes a wetness detector having at least two spaced apart electrodes. The medical system also includes a housing configured to be implanted in a patient, in some implementations. The housing contains the receiver, the generator, the energy cell, and the power consumption component. In some implementations, the receiver is configured to wirelessly receive energy from at least two distinct energy sources emitting distinct types of energy. In some implementations, at least one of the energy sources is a dialysis machine remote from the receiver. The medical system also includes a sensor coupled to the receiver and a controller coupled to the sensor, in particular implementations. The sensor is configured to sense a parameter related to the distinct types of energy. The controller is configured to tune one or more of the receiver and the generator to absorb or transform a selected type of energy. The controller may be configured to receive a plurality of receivers. In some implementations, the distinct types of energy are selected from the group consisting of: radiofrequency signals, thermal energy, light energy, and kinetic energy. The distinct type of energy may include radiofrequency signals, and wherein the receiver includes an antenna. In some implementations, the generator is configured to convert the radiofrequency signals to direct current. In some implementations, the distinct type of energy includes thermal energy, and the receiver includes a thermocouple. The generator may include a thermoelectric generator. In some implementations, the receiver is a non-inductive receiver. The medical system may house the energy cell in a liquid impervious housing. The energy cell includes a capacitor, in particular implementations. The distinct types of energy may include kinetic energy and the receiver may include a microelectromechanical system (MEMS) device. The generator may include a MEMS generator. In some implementations, the distinct type of energy includes light energy, and wherein the receiver includes a photosensor. In some implementations, the generator includes a photovoltaic cell. The medical system may include a programmable clock configured to tune one or more of the receiver and the generator based on a time of day. In some implementations, the medical system includes a controller coupled to the generator. The controller is configured to evaluate an efficiency of energy generation from each of the at least two distinct energy sources and to tune the receiver to receive a selected type of energy and the generator to generate the selected type of energy source. In some implementations, tuning includes shutting down one or more components of the receiver.

In another aspect of the invention, a dialysis system for wirelessly charging a portable medical device includes a sensor configured to detect a presence of the portable medical device and a transmitter configured to transmit radiofrequency signals from the dialysis system to the portable medical device to power a component of the portable medical device.

In another aspect of the invention a method of wirelessly charging a portable medical device includes detecting a presence of the portable medical device and transmitting radiofrequency signals from a dialysis machine to the portable medical device to power a component of the portable medical device.

In another aspect of the invention a method of wirelessly charging a portable dialysis device includes receiving radiofrequency signals from distinct energy sources remote from the portable dialysis device via a receiver of the portable dialysis device, converting the radiofrequency signals into electrical energy via a generator of the portable dialysis device, storing the electrical energy in an energy cell of the portable dialysis device, and powering a power consumption component of the portable dialysis device by transmitting the energy from the energy cell to the power consumption component.

Implementations can include one or more of the following advantages. In some implementations devices related to dialysis treatments can advantageously be charged wirelessly in a non-inductive manner. Wirelessly charging such devices utilizing multiple energy sources reduces battery size requirements and device size and/or precludes battery replacement to extend the operational lifetime time of such devices. The wireless charging methods provided by implementations disclosed herein may advantageously be facilitated by and during dialysis treatments. Implementations of the devices disclosed herein may be configured for wireless charging by multiple sources having distinct types of energy sources.

Wirelessly charging a medical device with distinct types of energy sources has multiple advantages. For example, wirelessly charging the device with thermal energy permits efficient recharging of wearable/implantable devices passively while the device is being worn by the user. Additionally, the ability to recharge the same device with multiple different types of energy decreases the likelihood of the power source becoming depleted due to a lack of rechargeable energy. For example, if the temperature differential between a patient's body and the ambient room temperature were insufficient to recharge the medical device thermally, charging via ambient or dedicated radiofrequency energy can be employed. Similarly, if ambient or dedicated radiofrequency energy sources for charging were out of range of the medical device but the patient was active or the device were positioned in the line of sight of the sun either or both kinetic energy and solar energy can be used to recharge the battery.

Other aspects, features, and advantages will be apparent from the description and drawings, and from the claims.

DETAILED DESCRIPTION

Figure 1A:
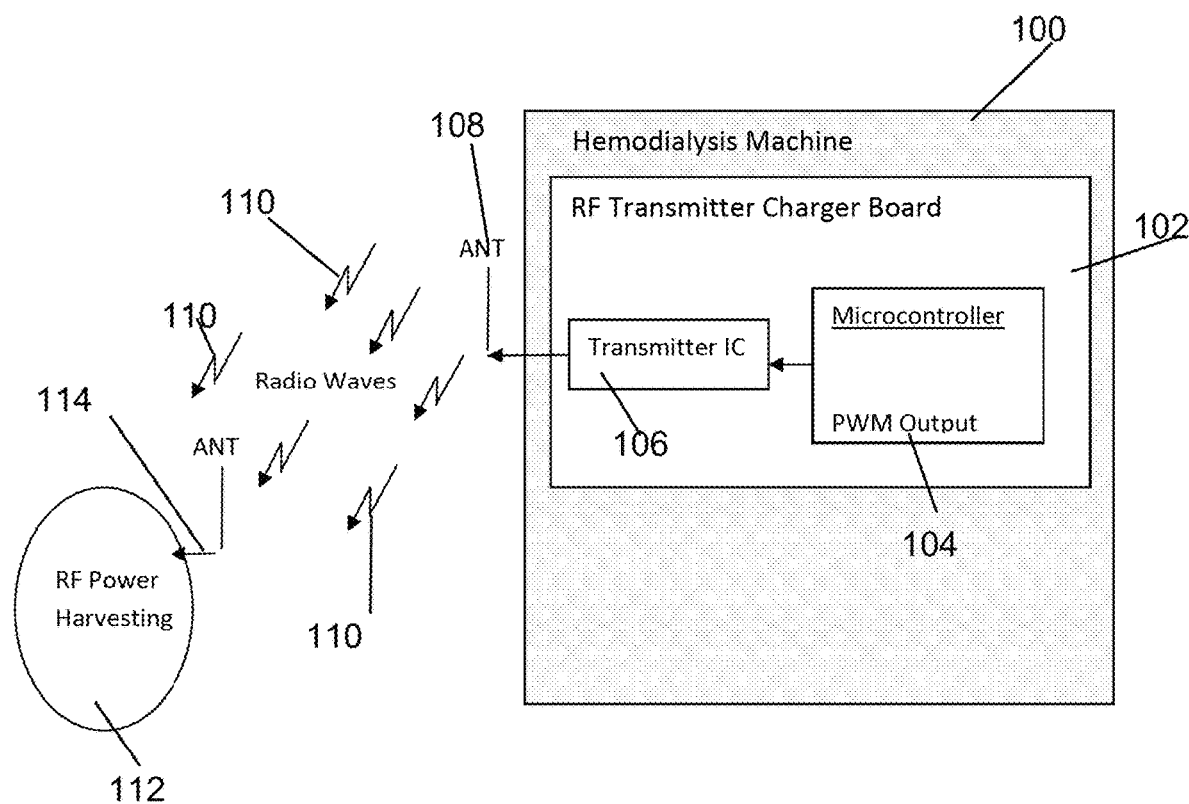
FIG. 1A shows a schematic diagram of a medical device wirelessly charging via radiofrequency transmissions from a hemodialysis machine.

FIG. 1A shows a schematic diagram of a medical device 112 wirelessly charging via radiofrequency transmissions from a dialysis machine, such as a hemodialysis machine 100. Although the system described herein is largely discussed in connection with hemodialysis systems by way of example, it is explicitly noted that the system described herein may be implemented in connection with other types of medical systems and treatments, including peritoneal dialysis (PD) systems. The hemodialysis machine 100 includes a transmitter system 102 for transmitting electromagnetic energy via radiofrequency signals 110. The transmitter system 102 transmits the radiofrequency signals 110 for receipt, conversion, and use by the medical device 112. The transmitter system 102 includes a transmitter integrated circuit 106 and a microcontroller 104 configured to control operation of the transmitter integrated circuit 106. The transmitter system 102 may be implemented via a circuit board installed in the hemodialysis machine. The transmitter system 102 includes a power circuit that supplies the microcontroller 104, an internal RF amplifier (not shown) and the antenna 108 of the transmitter integrated circuit 106 with power. The power circuit may be activated in concert with activation of the hemodialysis machine 100. The transmitter integrated circuit 106 includes an antenna 108 for sending the radiofrequency signals 110 to the medical device 112.

As discussed further herein, in certain implementations, the antenna 108 is configured to send and receive signals for sensing the presence of a medical device configured for wireless charging, for example, by detecting if the medical device 112 is within range of the hemodialysis machine 100 by sending and receiving a signal echoed by the medical device 112. The microcontroller 104 includes a timer, a clock, and/or other programmable components in certain implementations. The microcontroller 104 may be programmed for example to activate the transmitter integrated circuit 106 during a particular time of day or on a particular schedule. The microcontroller 104 is configured to detect certain operating conditions of the hemodialysis machine 100 in certain implementations. For example, in some implementations, the microcontroller 104 detects a pumping operation of the hemodialysis machine 100 to determine that a user and medical device 112 worn by a user are likely to be within range. In response to the microcontroller 104 detecting the pumping operation of the hemodialysis machine 100, the microcontroller 104 activates the transmitter integrated circuit 106 for transmission of radiofrequency signals 110 for receipt by the medical device 112. In certain implementations, the antenna 108 of the transmitter integrated circuit 106 is a 50 ohm antenna. The antenna 108 of the transmitter integrated circuit 106 may include a 4 watt transmitter. In certain implementations, the antenna 108 of the transmitter integrated circuit 106 is configured to transmit radiofrequency signals up to 50 feet. The transmitter system 102 may be configured to operate at frequencies including, but not limited to, 900, 1800, and 1900 MHz. The antenna 108 of the transmitter integrated circuit 106 may be configured to output high power radiofrequency signals at specific frequencies for the medical device 112.

Figure 1B:
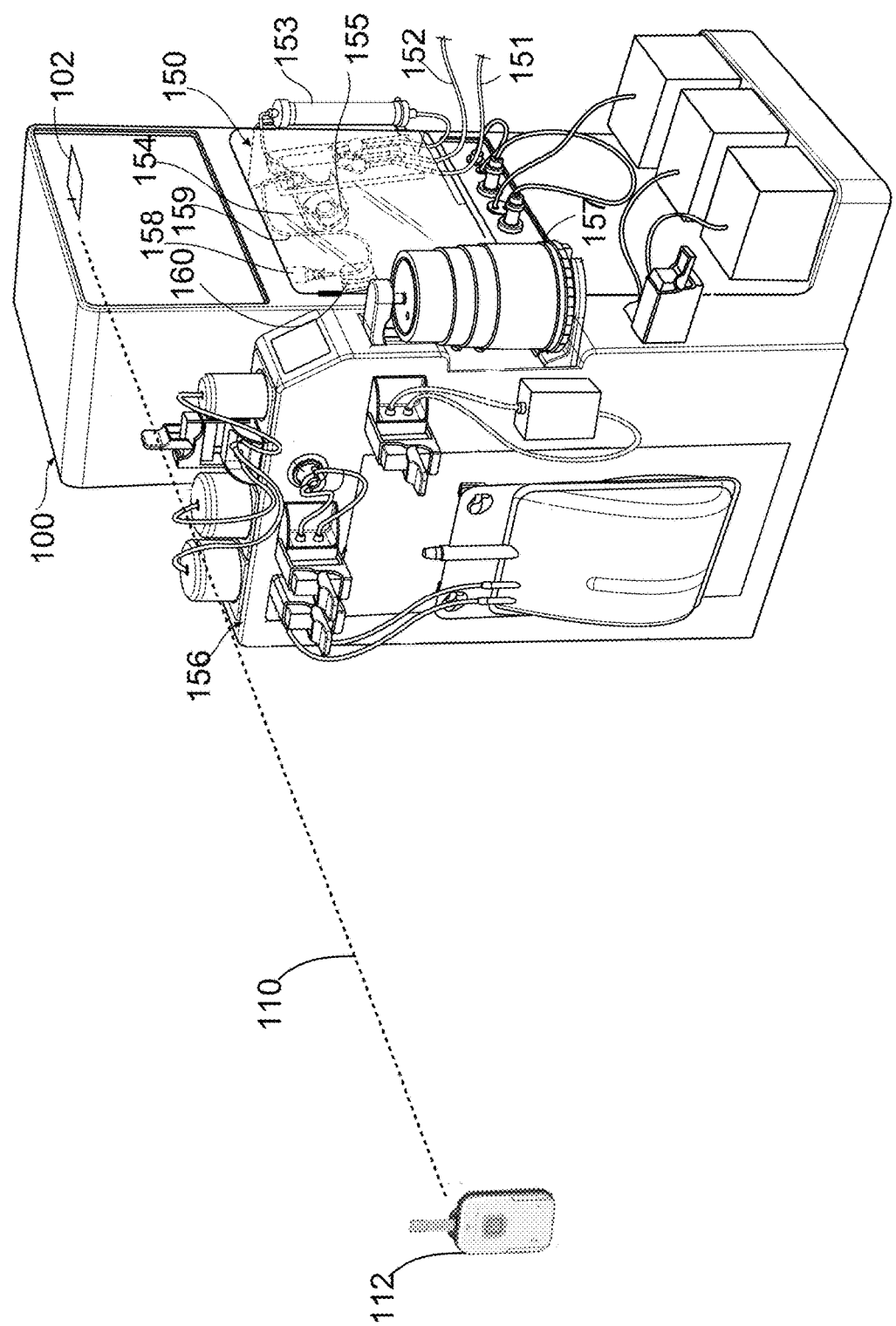
FIG. 1B shows an example of the medical device schematically illustrated in FIG. 1A wirelessly charging via radiofrequency transmissions from the hemodialysis machine.

FIG. 1B illustrates a hemodialysis system including the hemodialysis machine 100 housing the RF transmitter board 102 configured to provide radiofrequency signals 110 to the medical device 112 for wirelessly charging the medical device 112. As shown in FIG. 1A, the hemodialysis system includes a blood component set 150 secured to a front face of the hemodialysis machine 100. The blood component set 150 includes arterial and venous patient lines 151, 152 that are connected to a patient during treatment. The arterial patient line 151 is connected to an inlet port of a dialyzer 153 via a series of blood lines, and the venous patient line 152 is connected to an outlet port of the dialyzer 153 via a series of blood lines. A blood pump line 154 positioned between the arterial patient line 151 and the dialyzer 153 is operably connected to a peristaltic blood pump 155 extending from the front face of the hemodialysis machine 100. The peristaltic blood pump 155 can be operated to pump blood through the various blood lines and components of the blood component set 150. In particular, operation of the blood pump 155 draws blood from the patient through the arterial patient line 151. The blood continues through a series of blood lines and blood components (e.g., sensors) to the dialyzer 153. The blood exits the dialyzer 153 and passes through another series of blood lines and components (e.g., sensors) and then is returned to the patient via the venous patient line 152. During use of the hemodialysis machine 100, dialysate is pumped to the hemodialysis machine 100. The dialysate is then passed through a dialyzer 153 connected to the hemodialysis machine 100 at the same time that a dialysis patient's blood is passed through the dialyzer 153. As a result, toxins, such as urea, migrate across a permeable membrane (e.g., hollow fibers) of the dialyzer from the patient's blood to the dialysate, producing spent dialysate (i.e., dialysate that contains toxins removed from the patient's blood). The spent dialysate is pumped to a module 156 where it passes through a sorbent device 157, which removes toxins from the spent dialysate. As a result of chemical reactions that occur within the sorbent device 157, the recycled dialysate exiting the sorbent device 157 typically contains gas, such as carbon dioxide. The recycled dialysate is then forced from the module 156 and is cycled back through the dialysate circuit and reused to cleanse the dialysis patient's blood.

A dilution water container may be connected to the hemodialysis machine 100 via a fluid line. In some cases, certain substances, such as sodium, may be added to, rather than stripped from, the dialysate as the dialysate passes through the sorbent device 157.

As the blood is pumped through the various blood lines and components of the blood component set 150, it may be desirable to inject certain substances, such as drugs and/or saline into the blood lines. A drug vial 158 (e.g., a heparin vial) may be connected to one of the blood lines via a drug delivery line. The drug delivery line 159 may be threaded through a peristaltic drug pump 160, which can be used to deliver the drug to the blood circuit during treatment. A saline bag may also be connected to a blood line of the blood component set 150 via a priming line. This arrangement allows saline to be delivered through the blood circuit formed by the blood lines and components of the blood component set when desired.

Figure 2:
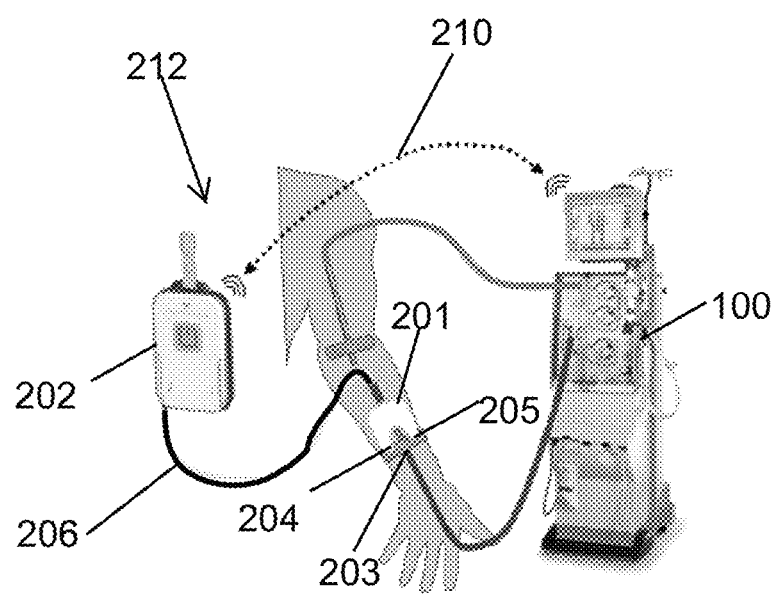
FIG. 2 illustrates a wetness detector configured for wireless charging.

While the hemodialysis machine 100 has been described as being used with a sorbent module 156, it should be understood that the dialysis machine 100 may also be of a type that does not use a sorbent module, as shown in FIG. 2.

As illustrated in FIG. 2, the medical device 112 may include a wetness detector 212, in accordance with certain implementations. The wetness detector 212 operates based on detecting conductivity of an electric circuit including spaced apart electrodes positioned in prongs 204 and 205 of the sensing pad 201 and electrically coupled to the control unit 202 via a wire 206. The sensing pad 201 may be applied directly to the skin in the area of a venous puncture site adjacent to the venous needle 203. The venous needle 203 is coupled to the hemodialysis machine 100. The sensing pad 201 can absorb blood leaking during dialysis treatment to provide an alert of a dislocation or leakage of the venous needle 203. The leaking blood changes the conductivity of the electric circuit positioned in the sensing pad 201. A current is provided to at least one of the spaced apart electrodes via an energy storage component of the wetness detector 212 and the conductivity between the electrodes is monitored via control unit 202. The control unit 202 houses the energy storage component, a generator system and a receiver system. The energy storage component includes a rechargeable battery in certain implementations. The rechargeable battery may be a thin-celled battery. The energy storage component includes a capacitor in certain implementations. The energy storage component is energized or charged and recharged via the generator system of the wetness detector 212. The generator system is coupled to the receiver system of the wetness detector 212. The receiver system housed in the control unit 202 receives energy via wirelessly transmitted radiofrequency signal 210 transmitted from the hemodialysis machine 100. In response to detecting a conductivity change between the spaced apart electrodes that exceeds a particular threshold, the control unit 202 wireless transmits an alarm signal to the hemodialysis machine 100. The alarm signal causes the extracorporeal circuit of blood flow to be stopped in certain implementations.

Figure 3:
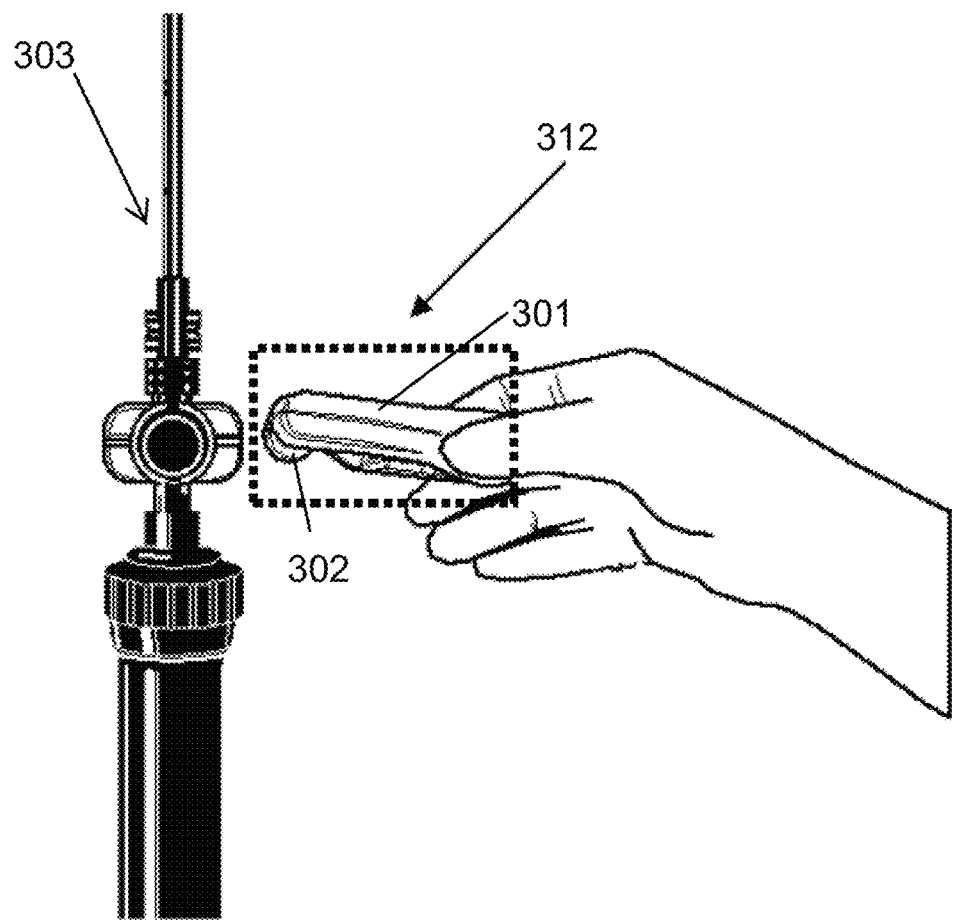
FIG. 3 shows a hematocrit detector configured for wireless charging.

In another implementation illustrated in FIG. 3, the medical device 112 includes a hematocrit detector 312. The hematocrit detector 312 includes a sensor clip 301 housing an electronic light emitter/detector unit in a head 302 of the sensor clip 301. The hematocrit detector is configured to test the percentage of red blood cells and provide a signal, wirelessly for example, indicating the results of the test. The hematocrit detector 312 detects the absorption and scattering properties of light transmitted through the whole blood as it flows through a disposable blood chamber 303. The disposable blood chamber 303 can be attached to the arterial side of a dialyzer during dialysis treatment. The sensor clip 301 locks into place around the blood chamber 303. In certain implementations, the hematocrit detector 312 includes a transmitter configured to provide wireless data signals to the hemodialysis machine 100.

The medical device 112 may include other blood filtration devices, blood monitoring components, or other devices related to dialysis treatments, in accordance with inventive implementations disclosed herein.

Figure 4:
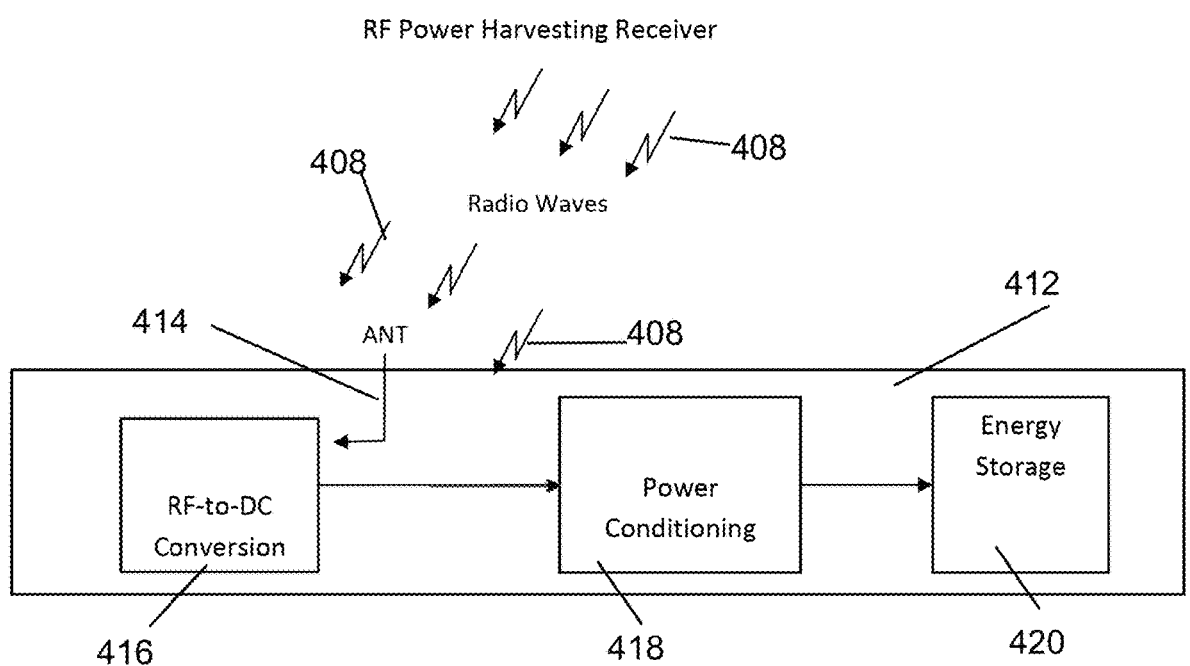
FIG. 4 shows a schematic diagram of wirelessly charging a medical device via ambient radiofrequency signals from various sources.

FIG. 4 shows a schematic diagram of wirelessly charging a medical device 412 via ambient radiofrequency signals 408 from various sources. FIG. 4 illustrates a conversion process implemented by a medical device, such as device 112 of FIGS. 1A and 1B. As illustrated in FIG. 4, an antenna 414 of the medical device 412 receives radiofrequency signals 408 from a radiofrequency source. As demonstrated in FIG. 4, the radiofrequency signals 408 may be received from one or more ambient sources generating radio waves generally for other purposes. The ambient sources include, but are not limited to, a mobile display device, a mobile phone, a wireless router, a mobile electronic device, a medical instrument, and other electronic devices transmitting radio waves. These ambient radio waves, while generally of less power than those received by a dedicated radiofrequency charging source as shown in FIGS. 1A and 1B, are received and processed in a similar manner. In particular, the radiofrequency signals 408 are received by the antenna 414, which transmits the signals 408 to an onboard power harvesting circuit 416 or RF generator that converts or transforms the radiofrequency signals to electrical energy such as direct current. The direct current created by the power harvesting circuit 416 may be conditioned to a specific voltage by a power conditioning components 418. The electrical energy from the power conditioning component 418 is then used to charge, energize, or recharge, the energy storage device 420, which includes an energy storage cell such as a thin cell battery or super-capacitor in certain implementations. The power consumption components, such as the electrodes, a controller, a processor, an actuator, a sensor or other components of the medical device 412 are configured to operate by consuming power, generally at a low rate, from the energy storage device 420.

Figure 5:
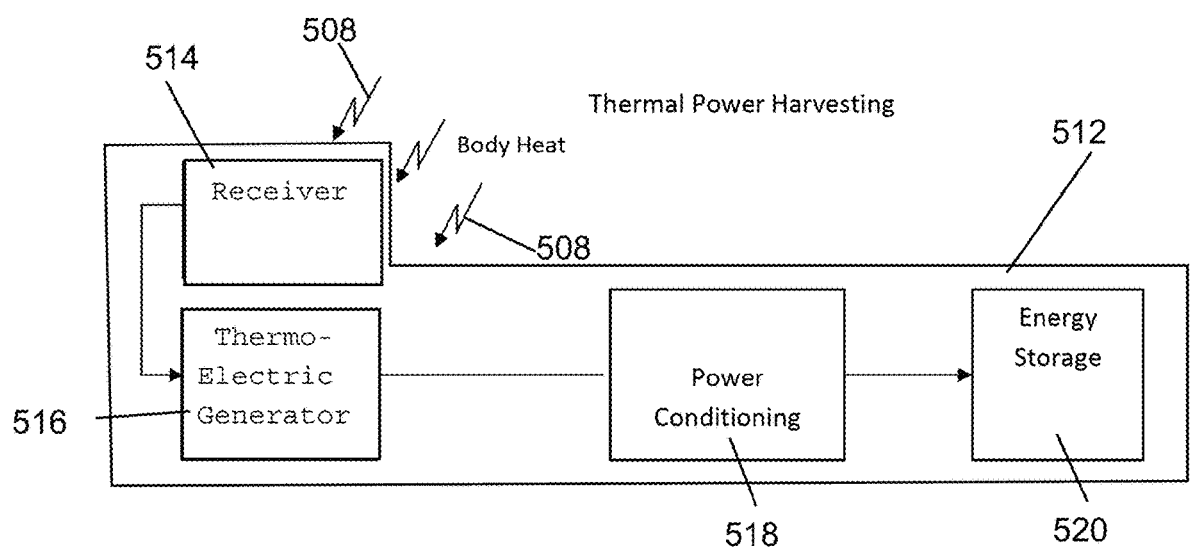
FIG. 5 shows a schematic diagram of wirelessly charging a medical device via thermal heat transmission.

In accordance with certain implementations, various implementations may harvest energy or receive energy in other forms in addition to or as an alternative to harvesting energy from dedicated or ambient radiofrequency energy sources. FIG. 5 shows a schematic diagram of wirelessly charging a medical device via thermal heat transmission. As discussed further herein, a medical device may be able to move between radiofrequency and thermal transmission and/or may be able to receive energy from distinct sources and/or distinct types of sources simultaneously. In thermal harvesting, the medical device 512 includes a receiver 514 configured to absorb thermal energy 508. The receiver 514 may include a thermocouple component. The thermocouple, which may be incorporated into a housing or enclosure of the medical device 512, absorbs heat from a source, such as the body of the patient and generates electrical energy by the thermoelectric effect. The receiver 514 that contacts the patient's skin on one side may be coupled to a thermoelectric generator 516, in the case of the mobile electronic device 512 embodied as a wearable device. The opposite side of the device 512 (i.e. the side opposite the side in contact with the patient's skin) is exposed to ambient temperatures. Accordingly, the side of the device in contact with the patient's skin may be at a temperature of 32-35 degrees Celsius while the ambient temperature in the room may be on the order of 20 degrees Celsius. The thermoelectric generator 516 uses this temperature difference to generate electricity. The thermoelectric generator 516 uses the same effect used by bimetallic thermocouples and can also be produced with thin-film semiconductors. When a thermal gradient is applied across oppositely doped semiconductors, it causes hot carriers to migrate through the material in the direction of the heat flux. If the p-type and n-type materials are electrically connected in series, then the carrier migration causes a voltage across the p-n couple, which can source power into an external load. The p-n couple's open circuit voltage increases linearly with the temperature differential and is small, in the range of 30 to 50 mV. The power generated is proportional to the square of the temperature differential. This is because the efficiency of the material, which is in the 1% to 2% range in certain implementations, increases with temperature.

In certain implementations, for example when encompassed in a wireless wetness detector, the enclosure of the medical device 512 may be used as thermal heat sink for the thermoelectric generator 516 in order to allow a higher conversion efficiency to charge the energy storage device 520. For example, the top and bottom sides of the enclosure may be made out of a thermally conductive plastic material. The bottom side of the enclosure increases the surface area in contact with the patient's skin, while the top side increases the surface area exposed to ambient air. The energy received by the receiver 514 is converted to direct current electrical energy by the thermoelectric generator 516. Once the thermal energy is converted to electrical energy, the electrical energy is conditioned, for example to a particular voltage or current, by power conditioning component 518. The power conditioning component 518 then transmits the conditioned electrical energy to the energy storage device 520 for storage and use later by a component of a medical device 512.

Figure 6:
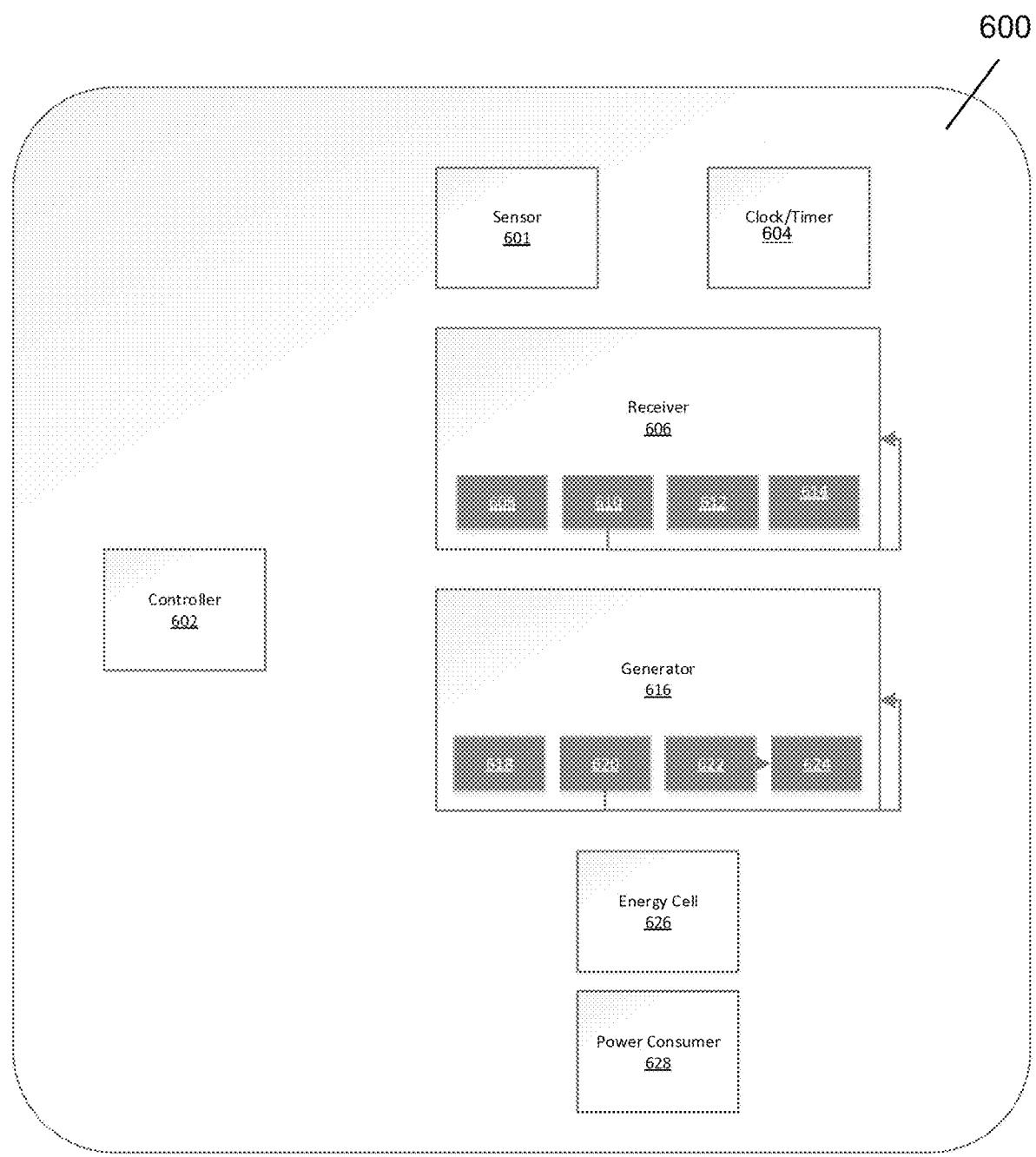
FIG. 6 illustrates a medical device configured for wireless charging via one or more distinct power sources.

FIG. 6 illustrates a medical device 600 configured for wireless charging via one or more distinct power sources, in accordance with inventive implementations. The medical device 600, which may include an implantable or wearable medical device, may include one or more systems, such as those demonstrated in FIGS. 1A-5 for harvesting energy from radiofrequency signals or thermal energy. The medical device 600 includes systems for harvesting or receiving other forms of energy, in accordance with certain implementations. The other energies include light energy, e.g. solar energy, and kinetic energy. The medical device 600 includes a controller 602, which may include one or more microprocessors configured to communicate with and collectively control components of the medical device 600. The controller 602 and the related electronic components may be electrically connected via a printed circuit board permitting bi-directional communications between the components. The controller 602 is communicably coupled to a sensor 601. The sensor 601 is configured to sense one or more conditions related to the type or types of energy harvested or received by the medical device 600. For example, the sensor 601 senses temperatures in certain implementations. In other implementations, the sensor 601 senses the signal strength and/or frequency of radiofrequency signals detected thereby. The sensor system 601 may also be able to sense accelerations, via an accelerometer, or light intensity or radiant energy via a lux meter, light detector, or an optical sensor. The measured parameter as detected by the sensor 601 is communicated to the controller 602, which uses the detected parameter to control other components, including but not limited to a clock 604, a receiver system 606, a generator system 616, an energy storage system 626, and a power consumption component 628.

The clock 604 is used to determine when various parameters are detected and is used to time the duration of such events or to time the operation of other components of the medical device 600. The timing information may be stored in a memory device communicably coupled to the controller 602. The clock 604 is also used to control the receiver system 606, the generator system 616, the energy storage system 626, and the power consumption component 628, in certain implementations. In particular implementations, the clock 604 may be programmed to generate energy during certain times of day and is configured to cause certain energy generation modes during certain times of day. For example, the clock 604 can allow thermal energy to be harvested while the wearer of the device is sleeping. In other example implementations, the clock 604 can allow solar energy to be harvested during peak daylight hours. Other information, such as dialysis times, may be preprogrammed into the controller 602 and/or clock 604 so that energy generation via a dedicated transmission source of a transmitter integrated circuit of a hemodialysis machine is controlled during treatment periods. Alternatively or additionally, the sensor 601 can sense transmissions from a dedicated transmission source and initiates power generation based on the sensed condition.

Still referring to FIG. 6, the receiver system 606 includes various receiver components including, but not limited to, a radiofrequency receiver antenna 608, a thermocouple 610, a photosensor 612, and a microelectromechanical system (MEMS) receiver 614. The radiofrequency receiver antenna 608 is for receiving radiofrequency signals. The thermocouple 610 is for receiving thermal energy. The photosensor 612 is for receiving light energy, e.g. solar energy. The MEMS receiver 614 is for receiving mechanical vibrations or kinetic energy.

The receiver system 606 is communicably coupled to the generator system 616, which includes one or more of a radiofrequency to DC converter component 618, a thermoelectric generator 620, a photovoltaic generator 622, and a MEMS generator 624 such as a piezoelectric generator or an electrostatic generator. The radiofrequency converter 618 converts radiofrequency energy received by the receiver 608 into electrical energy, such as direct current electrical energy. The thermoelectric generator 620 converts thermal energy, for example by the Peltier effect, received via the thermocouple 610 and converts it into electrical energy, such as direct current electrical energy. The photovoltaic generator 622 converts solar energy received via the photosensor 612 into electrical energy, such as direct current electrical energy. The MEMS generator 624 converts the kinetic energy received via the MEMS receiver 614 into electrical energy, such as direct current electrical energy. The electrical energy generated by the generator system 616 is transferred to an energy storage device 626. The energy storage device 626 may be implemented via a rechargeable battery, such as a thin cell battery, and/or may be implemented via a capacitor configured to store the energy charge.

The medical device 600 includes a power consumption device 628 that consumes the energy stored in the energy storage device 626. The power consumption device 628 may include one or more sensor components such as a hematocrit sensor, one or more electrodes of a wetness detector, a temperature sensor of an inline blood temperature sensor, or other components of a dialysis related component, in accordance with certain implementations.

The medical device 600 may be an implantable device configured for implantation in a human and the aforementioned components may be housed in an implantable housing in accordance with particular implementations. The medical device 600 may be a wearable device in certain implementations. The medical device 600 may include other electrical components such as a low power Bluetooth system for remote communications or an active or passive radiofrequency identification tag for communicating with one or more components such as the hemodialysis machine 100 or a mobile electronic device, such as a tablet, PC, mobile phone, or remote monitoring station. In addition to non-inductively and wirelessly receiving wireless power via radiofrequency from the remote device(s), the medical device 600 may also be configured to communicate performance information to the remote powering device(s) including, but not limited to, identification of power generation source or type, power capacity of the energy storage cell, energy storage quantity, energy storage usage, detection characteristics, and sensed parameters.

Figure 7:
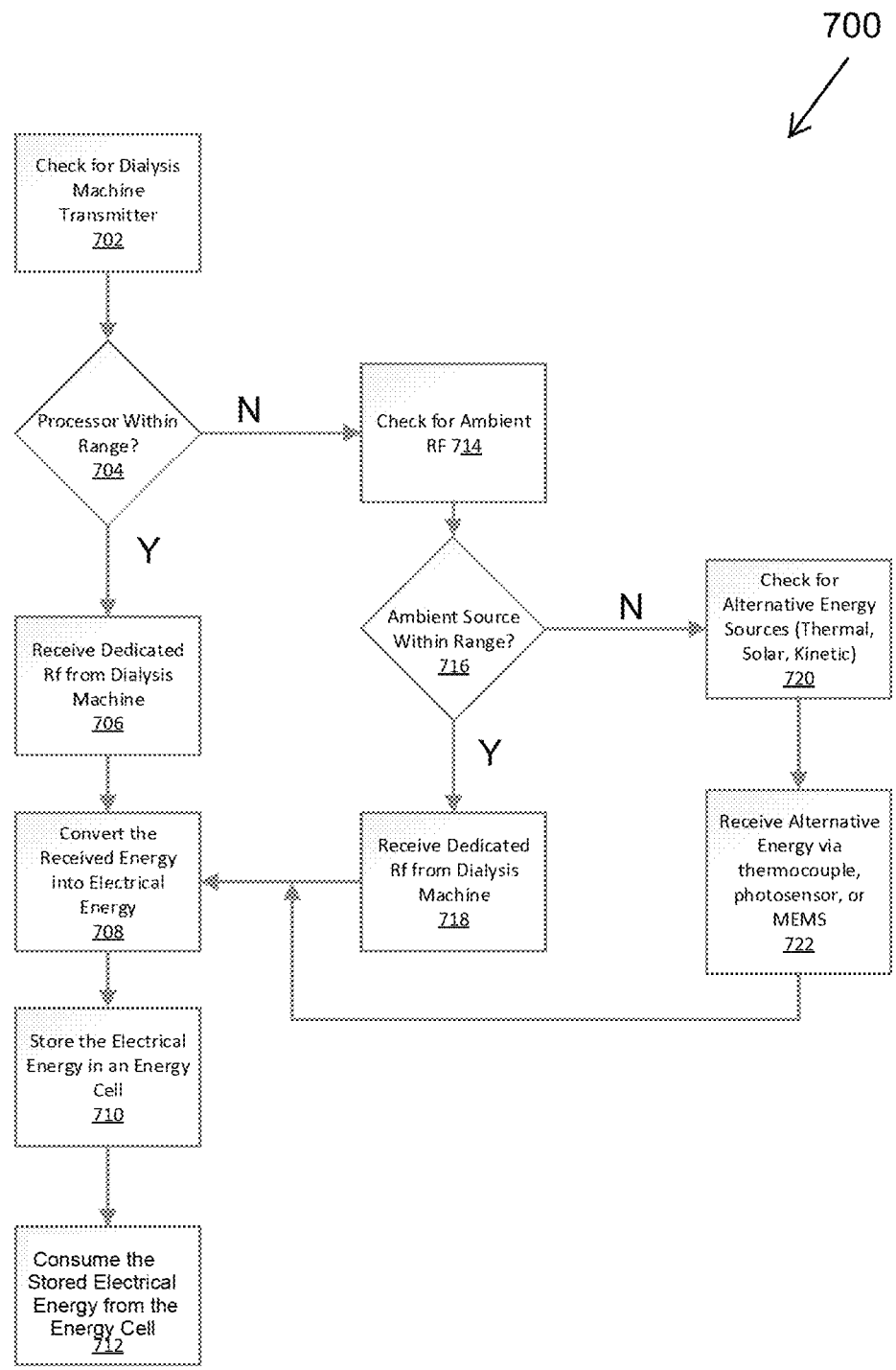
FIG. 7 is a flow diagram of a method of wirelessly charging a medical device.

FIG. 7 is a flow diagram of wirelessly charging a medical device in accordance with inventive implementations. The flow process 700 illustrated in FIG. 7 may be accomplished via a controller such as controller system 602 illustrated in FIG. 6. At 702, the controller checks for a dialysis machine (such as the hemodialysis machine 100 illustrated in FIGS. 1A and 1B) transmitting a dedicated radiofrequency signal for energy generation in the mobile electronic device. The check may include receiving transmission of a beacon signal and receiving or echoing of a return signal indicating reception of the transmitted signal. In analysis 704, the controller system determines if the dialysis machine is accessible or within range of the mobile electronic device. If the machine is available or within range, the controller initiates at 706 a process for receipt of radiofrequency transmission by the mobile electronic device. If the mobile electronic device detects the dialysis machine, an antenna is activated and/or configured to receive radiofrequency signals at a particular power that may be a higher power than the beacon signal (e.g., for example a beacon signal from the dialysis machine for identifying devices within range of the machine). The controller will proceed to convert the radiofrequency signals into electrical energy at 708. The controller will cause that electrical energy to be stored at 710 and used as necessary from the energy storage device by the medical device at 712. If the dedicated wireless charging power source (e.g. dialysis machine 100) is not available at analysis 704, the controller proceeds to check for available ambient radiofrequency signals at 714. If ambient energy sources are available as determined in analysis 716, the controller causes a receiver of the device to receive the ambient radiofrequency signals from one or more source via an antenna at 718 and proceeds to convert those ambient radiofrequency signals into electrical energy at 708. If no ambient energy source is available as determined at 716, the controller checks for one or more other energy sources at 720, such as thermal energy, light energy, or kinetic energy. Any or all available energy sources may be harvested or received by receiver (e.g. receiver 606) or the requisite receiver component at 722 and the energy received is converted at 708 for storage and usage in processes 710 and 712.

While the dialysis system has been principally described herein as being a hemodialysis system, other medical treatment systems can employ the techniques described herein. Examples of other medical treatment systems include peritoneal (PD) dialysis systems, hemofiltration systems, hemodiafiltration systems, apheresis systems, and cardiopulmonary bypass systems.

Implementations of the subject matter and the operations described in this specification can be implemented by digital electronic circuitry, or via computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus.

A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., a FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's user device in response to requests received from the web browser.

Implementations of the subject matter described in this specification can be implemented in a computing system that includes a back end component, e.g., as a data server, or that includes a middleware component, e.g., an application server, or that includes a front end component, e.g., a user computer having a graphical display or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include users and servers. A user and server are generally remote from each other and typically interact through a communication network. The relationship of user and server arises by virtue of computer programs running on the respective computers and having a user-server relationship to each other. In some implementations, a server transmits data (e.g., an HTML page) to a user device (e.g., for purposes of displaying data to and receiving user input from a user interacting with the user device). Data generated at the user device (e.g., a result of the user interaction) can be received from the user device at the server.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub combination. Moreover, although features may be described above as acting in certain combinations and even initially claimed as such, one or more features from a claimed combination can in some cases be excised from the combination, and the claimed combination may be directed to a sub combination or variation of a sub combination.

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be noted that the orientation of various elements may differ according to other exemplary implementations, and that such variations are intended to be encompassed by the present disclosure. It is recognized that features of the disclosed implementations can be incorporated into other disclosed implementations.

While various inventive implementations have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive implementations described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive implementations described herein. It is, therefore, to be understood that the foregoing implementations are presented by way of example only and that, within the scope of the appended claims and equivalents thereto, inventive implementations may be practiced otherwise than as specifically described and claimed. Inventive implementations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, the technology described herein may be embodied as a method, of which at least one example has been provided. The acts performed as part of the method may be ordered in any suitable way. Accordingly, implementations may be constructed in which acts are performed in an order different than illustrated, which may include performing some acts simultaneously, even though shown as sequential acts in illustrative implementations.

The claims should not be read as limited to the described order or elements unless stated to that effect. It should be understood that various changes in form and detail may be made by one of ordinary skill in the art without departing from the spirit and scope of the appended claims. All implementations that come within the spirit and scope of the following claims and equivalents thereto are claimed.

What is claimed is:

1. A method of charging a medical device comprising:
   receiving radiofrequency signals from a dialysis machine remote from the medical device via a receiver of the medical device, wherein the medical device comprises a detector;
   converting the radiofrequency signals into electrical energy via a generator of the detector;
   storing the electrical energy in an energy cell of the detector;
   powering an electric circuit of the detector by transmitting the energy from the energy cell to the electric circuit;
   detecting a parameter using the detector; and
   responsive to detecting the parameter, wirelessly transmitting a signal from the detector to the dialysis machine for controlling an operation of the dialysis machine.

2. The method of claim 1, wherein the operation of the dialysis machine comprises pumping blood.

3. The method of claim 1, wherein powering the electric circuit comprises applying power to an electrode of the detector to detect an electrical property related to a hematocrit level.

4. The method of claim 1, further comprising testing a property of blood with the medical device.

5. The method of claim 1, further comprising:
   receiving distinct energy types from distinct energy sources positioned remote from the detector via the receiver.

6. The method of claim 5, further comprising:
converting the distinct types of energy into electrical energy via the generator.

7. The method of claim 5, wherein receiving distinct energy types includes receiving energy selected from the group consisting of: radiofrequency signals, thermal energy, light energy, and kinetic energy.

8. The method of claim 7, wherein receiving distinct energy types includes receiving energy via a thermocouple.

9. The method of claim 7, wherein receiving distinct energy types includes receiving energy via a photosensor.

10. The method of claim 7, wherein receiving distinct energy types includes receiving energy via a microelectromechanical system (MEMS) device.

11. The method of claim 7, further comprising detecting a state of a wetness detector.

12. A medical system, comprising:
a receiver configured to wirelessly receive energy from at least one distinct energy source emitting a distinct type of energy;
a generator coupled to the receiver, the generator configured to convert the distinct type of energy into electrical energy;
an energy cell coupled to the generator, the energy cell configured to store the electrical energy;
a power consumption component comprising an electric circuit comprising a detector communicably coupled to the energy cell to consume the stored electrical energy; and
a wireless transmission system communicably coupled to the power consumption component and configured to transmit a signal to a dialysis machine from the detector for controlling an operation of the dialysis machine responsive to detecting a parameter using the detector.

13. The medical system according to claim 12, wherein the detector comprises a wetness detector having at least two spaced apart electrodes.

14. The medical system of claim 12, wherein the detector comprises a hematocrit detector.

15. The medical system according to claim 12, wherein the receiver is configured to wirelessly receive energy from at least two distinct energy sources emitting distinct types of energy.

16. The medical system according to claim 15, wherein at least one of the energy sources is the dialysis machine.

17. The medical system according to claim 15, further comprising:
a sensor coupled to the receiver, the sensor configured to sense a parameter related to the distinct types of energy; and
a controller coupled to the sensor, the controller configured to tune one or more of the receiver and the generator to absorb or transform a selected type of energy.

18. The medical system according to claim 15, wherein the distinct types of energy are selected from the group consisting of: radiofrequency signals, thermal energy, light energy, and kinetic energy.

19. The medical system according to claim 12, wherein the distinct type of energy includes radiofrequency signals, and wherein the receiver includes an antenna.

20. The medical system according to claim 19, wherein the generator is configured to convert the radiofrequency signals to direct current.

21. The medical system according to claim 12, wherein the distinct type of energy includes thermal energy, and wherein the receiver includes a thermocouple.

22. The medical system according to claim 21, wherein the generator includes a thermoelectric generator.

23. The medical system according to claim 12, wherein the receiver is a non-inductive receiver.

24. The medical system according to claim 12, wherein the medical system houses the energy cell in a liquid impervious housing.

25. The medical system according to claim 12, wherein the energy cell includes a capacitor.

26. The medical system according to claim 12, wherein the distinct type of energy includes kinetic energy, and wherein the receiver includes a microelectromechanical system (MEMS) device.

27. The medical system according to claim 26, wherein the generator includes a MEMS generator.

28. The medical system according to claim 12, wherein the distinct type of energy includes light energy, and wherein the receiver includes a photosensor.

29. The medical system according to claim 28, wherein the generator includes a photovoltaic cell.

30. The medical system according to claim 12, further comprising:
a programmable clock configured to tune at least one of the receiver and the generator based on a time of day.

31. The medical system according to claim 15, further comprising:
a controller coupled to the generator, the controller configured to evaluate an efficiency of energy generation from each of the at least two distinct energy sources and to tune the receiver to receive a selected type of energy and the generator to generate the selected type of energy source.

32. The medical system according to claim 31, wherein tuning comprises shutting down one or more components of the receiver.

33. A dialysis system for wirelessly charging a portable medical device, the dialysis system comprising:
a sensor configured to detect a presence of the portable medical device;
a transmitter configured to transmit radiofrequency signals from the dialysis system to the portable medical device to power an electric circuit of the medical device comprising a detector;
a receiver configured to receive a signal wirelessly transmitted from the portable medical device responsive to detection of a state of the medical device via the electric circuit; and
a controller configured to control an operation of the dialysis system in response to detection of a parameter using the detector.

* * * * *